United States Patent [19]
Umbaugh

[11] Patent Number: 5,899,879
[45] Date of Patent: May 4, 1999

[54] SPRING-ACTUATED NEEDLELESS INJECTOR

[75] Inventor: Jerald C. Umbaugh, Huntington Beach, Calif.

[73] Assignee: Genesis Medical Technologies, Inc., Denver, Colo.

[21] Appl. No.: 08/574,842

[22] Filed: Dec. 19, 1995

[51] Int. Cl.$^6$ .................................................. A61M 1/00
[52] U.S. Cl. .............................................. 604/68; 604/70
[58] Field of Search ................................ 604/68, 69, 70, 604/110, 162, 131, 134, 135

[56] References Cited

U.S. PATENT DOCUMENTS

| | | |
|---|---|---|
| Re. 24,419 | 1/1958 | Ziherl et al. . |
| 569,887 | 10/1896 | Richardson . |
| 2,547,099 | 4/1951 | Smoot . |
| 2,605,763 | 8/1952 | Smoot . |
| 2,635,601 | 4/1953 | May . |
| 2,645,223 | 7/1953 | Lawshe et al. . |
| 2,699,166 | 1/1955 | Dickinson, Jr. et al. . |
| 2,737,946 | 3/1956 | Hein, Jr. . |
| 2,764,977 | 10/1956 | Ferguson . |
| 2,800,903 | 7/1957 | Smoot . |
| 2,821,193 | 1/1958 | Ziherl et al. . |
| 2,821,981 | 2/1958 | Ziherl et al. . |
| 3,057,349 | 10/1962 | Ismach . |
| 3,115,133 | 12/1963 | Morando . |
| 3,138,157 | 6/1964 | Ziherl et al. . |
| 3,202,151 | 8/1965 | Kath . |
| 3,292,621 | 12/1966 | Banker . |
| 3,292,622 | 12/1966 | Banker . |
| 3,461,867 | 8/1969 | Zimmet et al. . |
| 3,688,765 | 9/1972 | Gasaway . |
| 3,695,266 | 10/1972 | Lussier . |
| 3,714,943 | 2/1973 | Yanof et al. . |
| 3,763,359 | 10/1973 | Cho et al. . |
| 3,788,315 | 1/1974 | Laurens . |
| 3,805,783 | 4/1974 | Ismach . |
| 3,815,594 | 6/1974 | Doherty . |
| 3,853,125 | 12/1974 | Clark et al. . |
| 3,859,996 | 1/1975 | Mizzy et al. . |
| 3,908,651 | 9/1975 | Fudge . |
| 3,933,155 | 1/1976 | Johnston . |
| 3,945,379 | 3/1976 | Pritz et al. . |
| 3,945,383 | 3/1976 | Bennett et al. . |
| 4,004,575 | 1/1977 | Sarstedt . |
| 4,031,889 | 6/1977 | Pike . |
| 4,059,107 | 11/1977 | Iriguchi et al. . |
| 4,089,334 | 5/1978 | Schwebel et al. . |
| 4,103,684 | 8/1978 | Isamach . |
| 4,124,024 | 11/1978 | Schwebel et al. . |
| 4,128,098 | 12/1978 | Bloom et al. . |
| 4,301,795 | 11/1981 | Zimmermann . |
| 4,329,988 | 5/1982 | Sarnoff et al. . |
| 4,342,310 | 8/1982 | Lindmayer et al. . |
| 4,400,172 | 8/1983 | Dettbarn et al. . |
| 4,403,609 | 9/1983 | Cohen . |
| 4,403,989 | 9/1983 | Christensen et al. . |

(List continued on next page.)

*Primary Examiner*—Manuel Mendez
*Attorney, Agent, or Firm*—Knobbe, Martens, Olson & Bear, LLP

[57] ABSTRACT

A needleless injector for injecting medication through the skin of a patient includes a vial which holds a volume of liquid medication. The vial includes a vial piston which moves to force the liquid medication out of the vial. A power mechanism applies force to the vial piston. The power mechanism includes a power piston which has a plurality of ratchets. A spring is positioned to apply force to the power piston. A trigger engages the ratchets on the power piston to hold the power piston in place against the force applied by the spring. The trigger selectively releases the power piston so that the power piston moves in response to the force applied by the spring. The power piston applies the force to the vial piston to cause the vial piston to force the liquid medication out of the vial. A cocking mechanism applies force to the power piston to move the power piston against the force of the spring to engage the ratchets. A travel adjustment mechanism is moveable to position the spring within the power mechanism to control the movement of the power piston and to thereby control the volume of liquid ejected from the vial.

5 Claims, 13 Drawing Sheets

U.S. PATENT DOCUMENTS

| | | |
|---|---|---|
| 4,421,508 | 12/1983 | Cohen . |
| 4,447,225 | 5/1984 | Taff et al. . |
| 4,475,905 | 10/1984 | Himmelstrup . |
| 4,507,113 | 3/1985 | Dunlap . |
| 4,518,385 | 5/1985 | Lindmayer et al. . |
| 4,592,742 | 6/1986 | Landau . |
| 4,596,556 | 6/1986 | Morrow et al. . |
| 5,106,371 | 4/1992 | Zhao et al. ............................. 604/110 |
| 5,211,628 | 5/1993 | Marshall ................. 604/110 |
| 5,312,348 | 5/1994 | Sans ....................... 604/110 |
| 5,527,284 | 6/1996 | Ohnemus et al. ..................... 604/110 |
| 5,531,705 | 7/1996 | Alter et al. ......................... 604/110 X |
| 5,556,384 | 9/1996 | da Encarnação ....................... 604/110 |
| 5,569,203 | 10/1996 | Chen ..................... 604/110 |
| 5,575,774 | 11/1996 | Chen ..................... 604/110 |
| 5,578,015 | 11/1996 | Robb .................. 604/110 X |

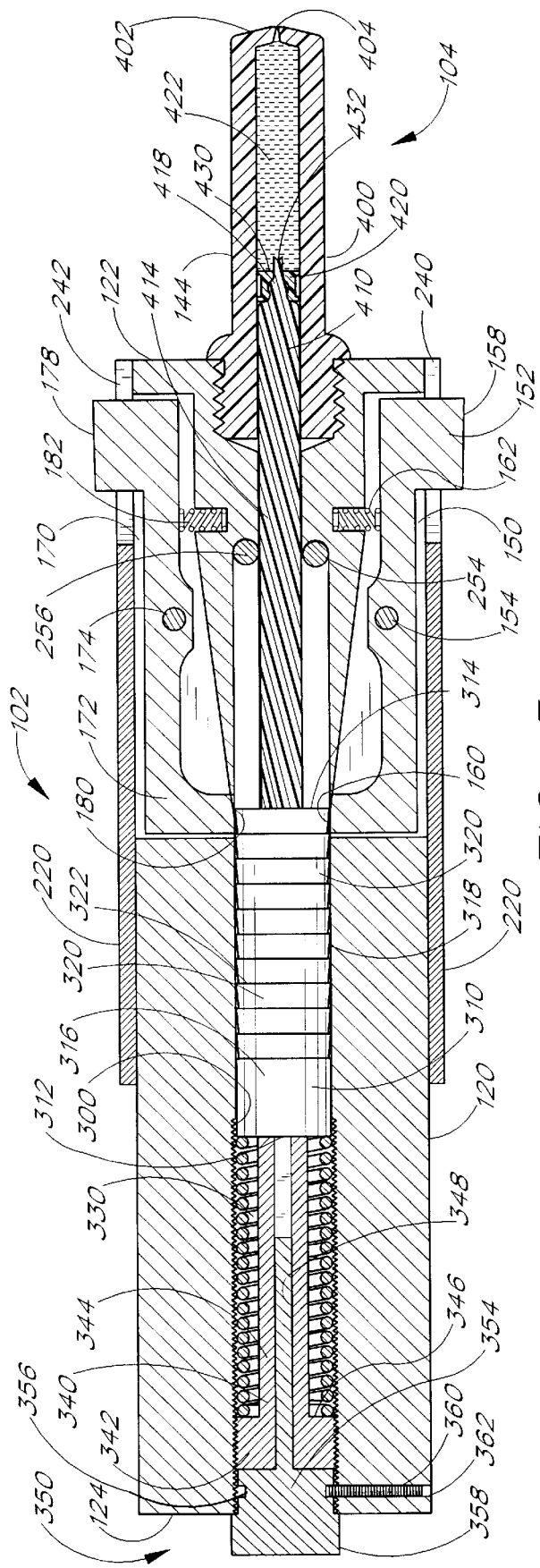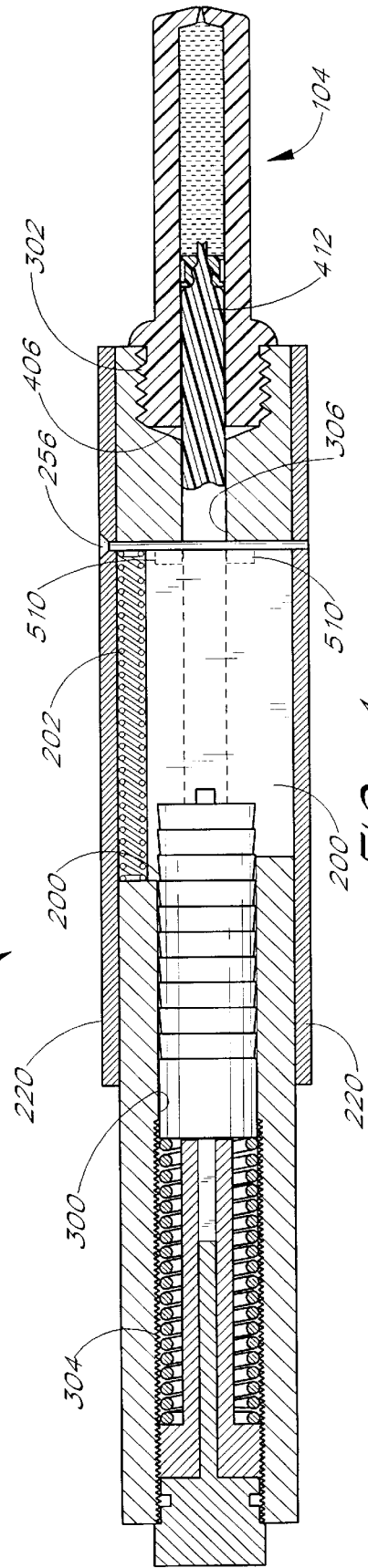
FIG. 3
FIG. 4

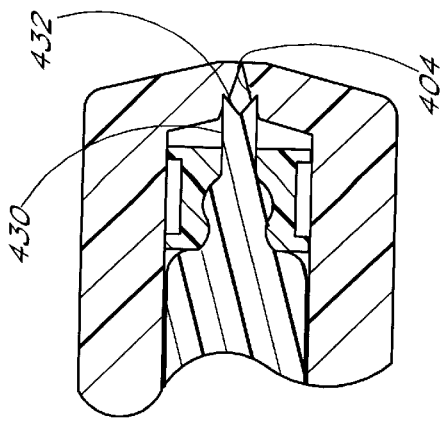
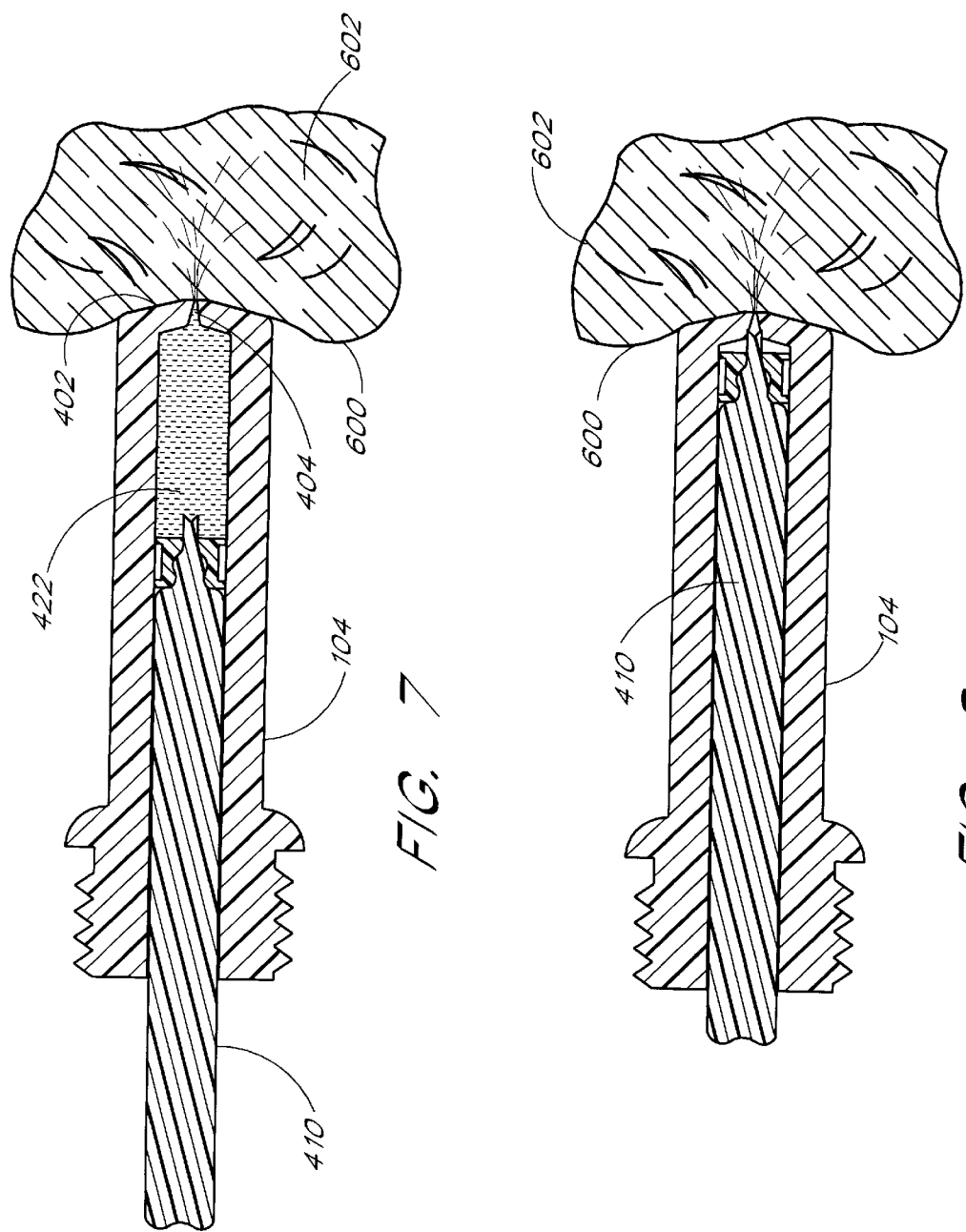
FIG. 7
FIG. 8
FIG. 9

SPRING-ACTUATED NEEDLELESS INJECTOR

BACKGROUND OF THE INVENTION

1. Field of the Invention

The present invention is directed to the field of medicinal injectors, and, more particularly, to needleless injectors which have spring-actuated pistons which force medicinal fluids through the skin without piercing the skin.

2. Description of the Related Art

Many systems have been developed for injecting liquid medications into persons as part of a treatment program, as vaccination against disease, and for other purposes. Many such medications are injected into the tissues under the skin rather than directly into a blood vessel. The medications thus injected are then absorbed by the circulatory system and transported throughout the body. Such intramuscular injections are used, for example, in the treatment of diabetes. Typically, an injection is made using a hypodermic syringe having a needle which pierces the skin so that the medication forced from the syringe is injected into the underlying tissue.

For many persons, the very thought of receiving an injection in this manner is uncomfortable at best and often frightening. Thus, needleless injectors have been developed to obviate the use of needles. Such needleless injectors apply a high pressure to a medicinal fluid in a syringe to force the fluid out of a small orifice at the end of the syringe. When the orifice of the syringe is held against the skin, the fluid penetrates the skin and enters the underlying tissues where it is absorbed as discussed above.

Various systems for applying the pressure to the fluid in the syringe have been developed. Some needleless injectors have used high pressure gas, such as, for example, carbon dioxide ($CO_2$). Other injectors have used springs to force the fluid out of the syringe. The present invention is directed to improvements to spring actuated needleless injectors.

SUMMARY OF THE INVENTION

One aspect of the present invention is a needleless injector which injects medication through the skin of a patient. The needleless injector comprises a vial which holds a volume of liquid medication. The vial comprises a vial piston which moves to force the liquid medication out of the vial. A power mechanism applies force to the vial piston. The power mechanism comprises a power piston which has a plurality of ratchets formed thereon. A spring has a first end and a second end, wherein the first end of the spring is positioned to apply force to the power piston. A trigger engages the ratchets on the power piston to hold the power piston in place against the force applied by the spring. The trigger selectively releases the power piston to move in response to the force applied by the spring. The power piston applies the force to the vial piston to cause the vial piston to force the liquid medication out of the vial. A cocking mechanism applies force to the power piston to move the power piston against the force of the spring to engage the ratchets. A travel adjustment mechanism is moveable to position the second end of the spring within the power mechanism to control the movement of the power piston, thereby controlling the volume of liquid ejected from the vial. Preferably, the travel adjustment mechanism comprises a threaded plug, and the power mechanism comprises a threaded bore. The threaded plug is rotatable in the bore to move the threaded plug closer to and further away from the vial to thereby limit the distance by which the power piston can be moved away from the vial when cocked. Also preferably, the ratchets on the power piston are spaced apart by equal distances, with each of the ratchets corresponding to an incremental volume of the vial. In particularly preferred embodiments, the travel adjustment mechanism is adjustable for a predetermined volume of liquid medication to cause the power piston to engage the vial piston to prevent a vial from being inserted into the power mechanism with a volume of liquid medication greater than the predetermined volume.

Another aspect of the present invention is a medication vial for needleless injection of a liquid medication into a patient. The medication vial comprises a container which defines a volume which receives a quantity of liquid medication. The container has a first end and a second end, and the first end has an orifice formed therein to release the liquid medication. A piston having a first end and a second end moves within the container. The first end of the piston is moveable with respect to the first end of the container to define the volume when the first end of the piston is moved away from the first end of the container. The piston forces the liquid medication through the orifice when the first end of the piston is moved toward the first end of the container. The first end of the piston has a protuberance formed thereon which closes the orifice to block further use of the container after the liquid medication is expelled.

Another aspect of the present invention is a stroke adjustment mechanism in a spring-powered needleless injector. The needleless injector has a piston, a spring to power the piston, and a trigger mechanism to selectably hold the piston against the spring and to release the piston to move in response to force provided by the spring. The piston is coupled to a vial of liquid medication to force liquid medication from the vial. The stroke adjustment mechanism comprises a plurality of ratchets formed on the piston. Each ratchet is selectably engageable with the trigger mechanism to select a stroke distance for the piston. An adjustment plug is moveable within the needleless injector. The adjustment plug is engageable with a first end of the spring and with a first end of the piston to control an amount of compression of the spring when the piston is engaged with the trigger mechanism. The adjustment plug further limits an amount of travel of the piston to thereby limit an amount of liquid medication ejected from the vial. Preferably, the adjustment plug comprises a threaded portion and an extended portion. The threaded portion has a shoulder which engages the spring. The extended portion engages the piston such that the spring is compressed between the piston and the shoulder. Also preferably, the extended portion of the adjustment plug includes a central bore. The stroke adjustment mechanism further includes an adjustment knob. The adjustment knob includes a manual engagement portion rotatable by a user and an extended portion. The extended portion of the adjustment knob engages the central bore of the extended portion of the adjustment plug to thereby rotate the adjustment plug when the engagement portion is rotated.

BRIEF DESCRIPTION OF THE DRAWINGS

The present invention will be described below in connection with the accompanying drawing figures in which:

FIG. 3 is a cross-sectional view of the needleless injector of FIGS. 1 and 1A taken along the lines 3—3 in FIG. 1, showing the needleless injector with a vial of having a substantially full volume of liquid in position and with the power mechanism cocked for operation;

FIG. 4 is a cross-sectional view of the needleless injector of FIGS. 1 and 1A taken along the lines 4—4 in FIG. 1A, showing the needleless injector with a vial of liquid in position and with the power mechanism cocked for operation;

FIG. 7 is an enlarged cross-sectional view of the vial of FIG. 1 in position against the skin of a patient pictorially illustrating the flow of the liquid medicine into the tissues of the patient;

FIG. 8 is an enlarged cross-sectional view of the vial as in FIG. 6 showing the plugging effect of the end of the piston to preclude further use of the vial;

FIG. 9 is an enlarged cross-sectional view of the end of the vial in FIG. 8 showing the plugging effect in more detail;

DETAILED DESCRIPTION OF THE PREFERRED EMBODIMENT

Figure 1:
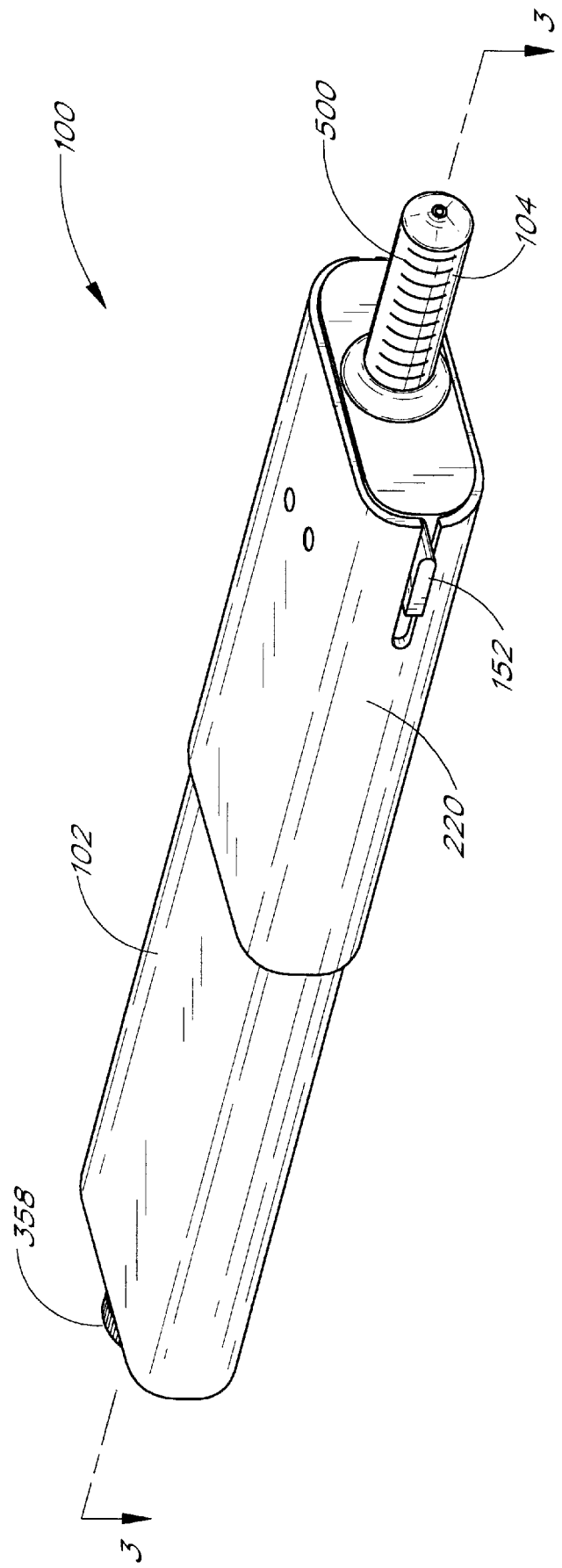
FIGS. 1 and 1A illustrate perspective views of the needleless injector of the present invention.
Figure 1A:
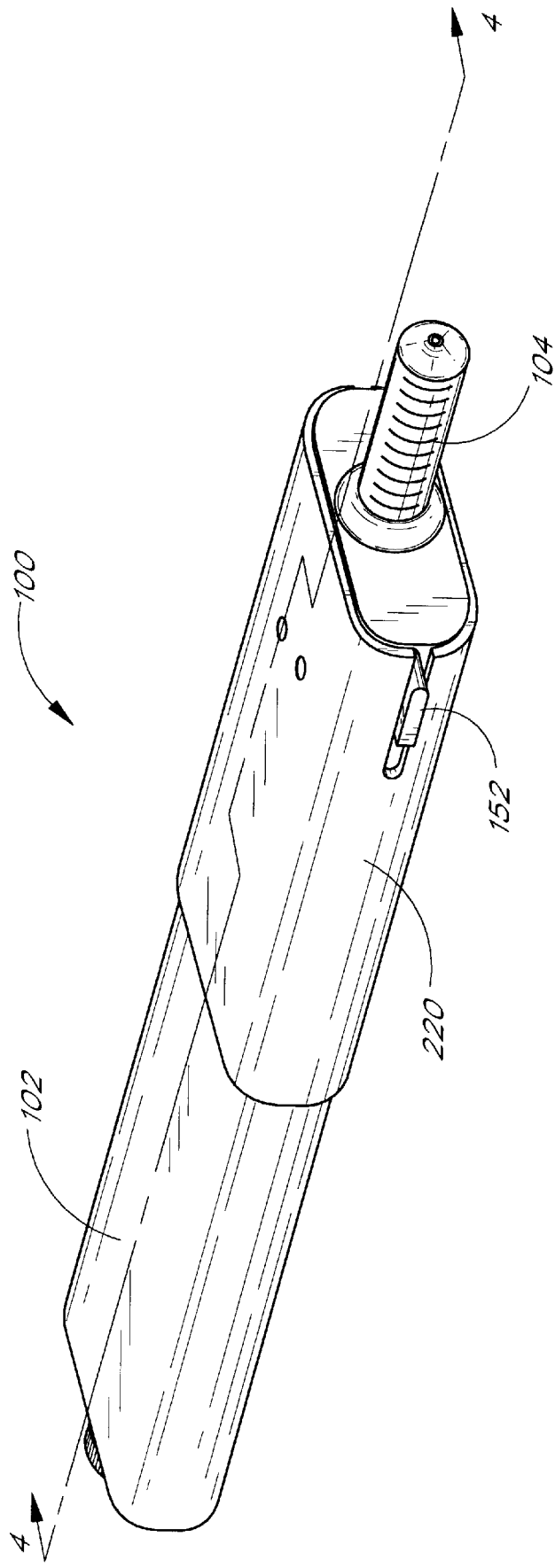

FIGS. 1 and 1A illustrate perspective views of a preferred embodiment of a needleless injector 100 in accordance with the present invention. (FIG. 1A is substantially the same as FIG. 1 and is included to provide the section lines for FIG. 4.) The needleless injector 100 comprises a power mechanism 102 and a medication vial 104. As illustrated in the exploded perspective view in FIG. 2, the medication vial 104 includes a threaded portion 106 which threadingly engages a threaded socket 108 of the power mechanism 102.

Figure 2:
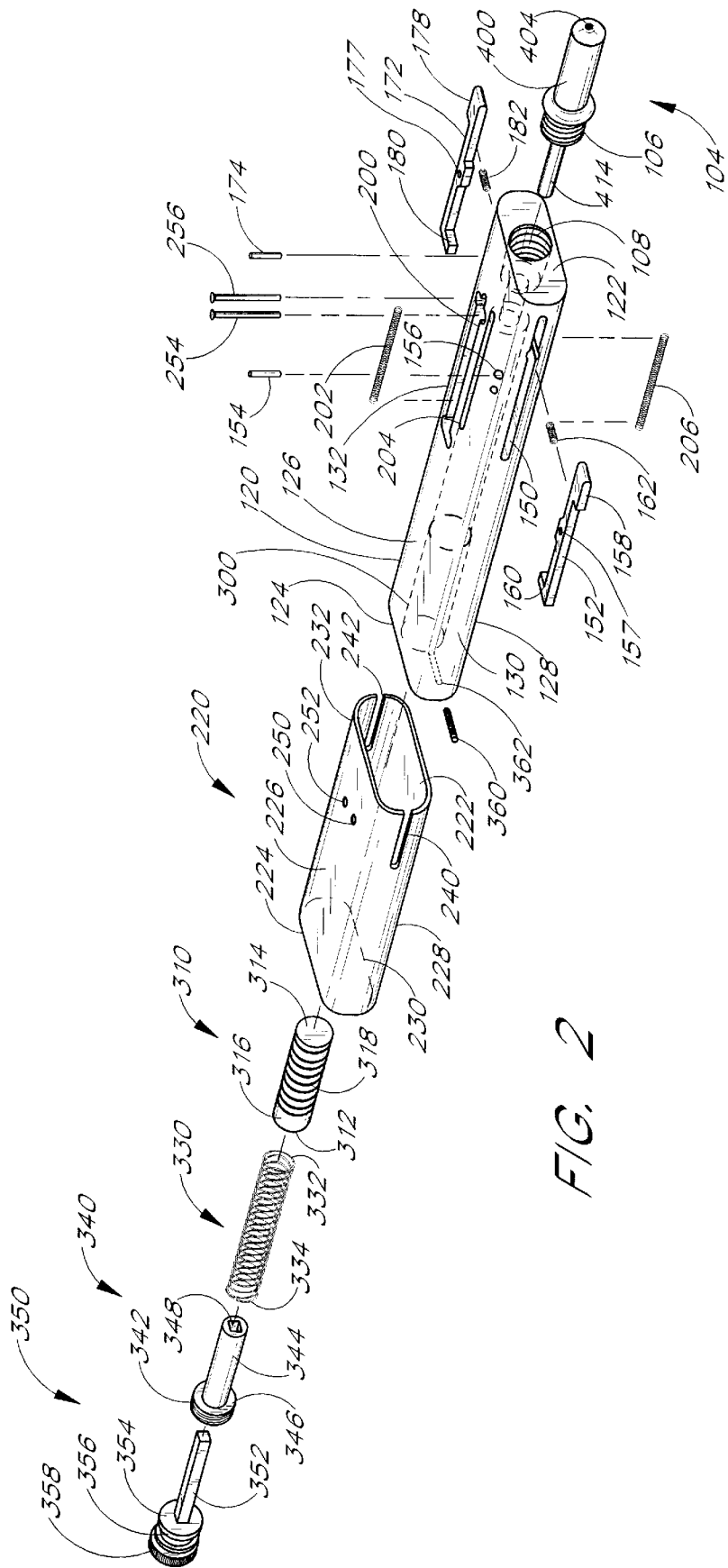
FIG. 2 illustrates an exploded view of the needleless injector of the present invention.

As shown more clearly in FIG. 2, the power mechanism 102 further includes a bar-shaped main body portion 120 which has a generally oval-shaped cross-section. The main body portion 120 is shown lying on its side in FIGS. 1 and 2 wherein an oval-shaped top end 122 has the socket 108 which receives the medication vial 104. The body portion 120 has an oppositely disposed oval-shaped bottom end 124. The body portion 120 has a first wide side 126 and an oppositely disposed second wide side 128. The body portion 120 has a first narrow side 130 and an oppositely disposed second narrow side 132.

A first trigger slot 150 is formed in the first narrow side 130 to receive a first trigger 152. As shown more clearly in FIG. 3, the first trigger 152 is pivotably mounted proximate to its midpoint on a pin 154 which is pressed into a hole 156 through the first wide side 126, through a hole 157 in the trigger 152, and into a corresponding hole (not shown) in the second wide side 128. The first trigger 152 has an activation portion 158 and a ratchet portion 160. A spring 162 biases the first trigger 152 so that the activation portion 158 is forced out of the first narrow side 130 and so that the ratchet portion 160 is forced into the first narrow side 130.

Similarly, a second trigger slot 170 is formed in the second narrow side 132 to receive a second trigger 172. The second trigger 172 is pivotably mounted on a pin 174 which is pressed into a hole (not shown) through the second wide side 128, through a hole 177 in the trigger 172, and into a corresponding hole (not shown) in the second wide side 128. The second trigger 172 has an activation portion 178 and a ratchet portion 180. A spring 182 biases the second trigger 172 so that the activation portion 178 is forced out of the second narrow side 132 and so that the ratchet portion 180 is forced into the second narrow side 132.

A slot 200 is formed into the first wide side 126. The slot 200 has a width on the first wide side 126 sufficient to receive a first sleeve spring 202. The width of the slot 200 at the first wide side 126 extends for a depth slightly greater than the diameter of the first sleeve spring 202 so that the first sleeve spring 202 can be positioned in the slot 200 without an portion extending above the first wide side 126. The width of the slot 200 narrows below the first sleeve spring 202 to a width less than the diameter of the first sleeve spring 202 so that first sleeve spring 202 is supported just below the first wide side 126. The narrow portion (not shown) of the first slot 200 extends through the body portion 120 to the second wide side 128.

A slot 204 substantially similar to the slot 200 is formed into the second wide side 128 to receive a second sleeve spring 206. The wide portion of the second slot 204 is not shown. The narrow portion of the second slot 204 is shown extending through the first wide side 126.

With the sleeve springs 202 and 206 in position, a cocking sleeve 220 is positioned over the body portion 120. The cocking sleeve 220 has a generally oval-shaped cross-section and is sized so that it fits over the body portion 120 and moves freely thereon from the top to the bottom without significant lateral play. The cocking sleeve has a top end 222, a bottom end 224, a first wide side 226, a second wide side 228, a first narrow side 230 and a second narrow side 232. A pair of slots 240 and 242 formed on the first narrow side 230 and the second narrow side 232, respectively, of the cocking sleeve 220 proximate to the top end 222. The slots 240, 242 have a sufficient width to encompass the activation portions 158 and 178 of the first trigger 152 and the second trigger 172, respectively. The cocking sleeve 220 further includes a pair of holes 250 and 252 extending from the first wide surface 226 to the second wide surface 228. When the cocking sleeve is in position on the body portion 120, the holes 250 and 252 are aligned with the ends of the slots 200 and 204, respectively. A pair of pins 254 and 256 are positioned in the holes 250 and 252, and extend thus through the slots 200 and 204. The pins 254 and 256 engage respective first ends of the sleeve springs 202 and 206. The operation of the cocking sleeve 220 and the sleeve springs 202 and 206 will be discussed below.

As shown in the cross-sectional views in FIGS. 3 and 4, the body portion 120 has a cylindrical bore 300 extending from the bottom end 124 to the top end 122. An upper portion 302 of the cylindrical bore 300 proximate to the top end 122 has a largest diameter and is threaded to form the socket 108 which receives the medication vial 104. A lower portion 304 of the cylindrical bore 300 proximate to the bottom end 124 a slightly smaller diameter. A lowermost portion of the lower portion 304 is threaded to receive an adjustment plug described below. A second portion of the lower portion 304 is not threaded. A middle portion 306 of the cylindrical bore 300 just below the upper portion 302 (i.e., to the left of the upper portion 302 in FIGS. 3 and 4) has a smaller diameter sized to receive a vial piston described below.

A piston 310 is positioned in the central bore 300. The piston 310 has a first end 312 and a second end 314. The first end 312 is positioned in the direction toward the bottom end 124 of the body portion 120, and the second end 314 is positioned in the direction of the top end 122. The piston 300 has an outside diameter selected to be slightly smaller than the inside diameter of the cylindrical bore 300 so that the piston 310 moves freely within the cylindrical bore 300 without significant play.

A first portion 316 of the piston 310 proximate to the first end 312 is generally smooth. A second or ratchet portion 318 of the piston 310 proximate to the second end 318 is milled or otherwise shaped to form a series of ratchets 320. In particular, the ratchet portion 318 shown in FIG. 3 has ten ratchets 320 formed thereon. Each of the ratchets 320 is tapered inward in the direction of the bottom end 124 of the body portion 120 to form a shoulder 322. As illustrated in FIG. 3, the ratchet portions 160 and 180 of the first trigger 152 and of the second trigger 172 are formed at an angle to generally match the taper of the ratchets 320 and to engage the shoulders 322. The operation of the ratchet portion 318 of the cylinder 310 with respect to the triggers 152 and 172 will be explained below.

A compression spring 330 is positioned in the cylindrical bore 300 below the piston 310. A first end 332 of the compression spring 330 rests against the first end 312 of the piston 310. A second end 334 of the compression spring 330 is positioned in a direction toward the bottom end 124 of the body portion 120.

A stroke adjustment plug 340 is positioned in the cylindrical bore 300 below the compression spring 330. The stroke adjustment plug 340 has a first portion 342 having a threaded outside diameter sized to fit within the cylindrical bore 300 and to engage the threaded portion of the cylindrical bore proximate to the bottom end 124 of the body portion 120. The stroke adjustment plug 340 has a second extended portion 344 which extends from the first portion 342 in the direction toward the top end 122 of the body portion 120. The compression spring 330 is positioned over the extended portion 344 such that the second end 334 of the compression spring 330 rests against a shoulder 346 of the first portion 342 of the stroke adjustment plug 340.

The stroke adjustment plug 340 has a central bore 348 formed therein. The central bore 348 of the stroke adjustment plug 340 preferably has a square cross section or any other non-circular cross section for the reasons set forth below. A stroke adjustment knob 350 is mounted in the cylindrical bore 300 proximate to the bottom end 124. A first portion 352 of the knob 350 is a generally square bar portion which has a cross section sized to fit within the central bore 348 of the stroke adjustment plug 340. A second portion 354 of the knob 350 is generally cylindrical and is sized to fit within the cylindrical bore 300 of the body portion 120. The second portion 354 has a groove 356 formed therein. As shown in FIG. 3, a set screw 360 is positioned through a hole 362 in the first side 130 of the body portion 120 to engage the groove 356 in the second portion 354 of the knob 350. The set screw 360 is initially threaded into the hole 362 sufficiently far to hold the knob 350 so that the second portion 354 cannot be removed from the cylindrical bore 300 but not so far as to press against the inside diameter of the groove 356. Thus, the knob 350 can turn within the cylindrical bore 300.

A third portion 358 of the knob 350 is generally cylindrical and has a size greater than the size of the cylindrical bore 300. The third portion 358 has a shoulder thereon which rests against the bottom end 124 of the body portion when the second portion 354 is inserted into the cylindrical bore 300. The outside diameter of the third portion 358 is preferably knurled to provide a surface which can be readily gripped by a person's fingers so that the knob 350 can be turned. As will be discussed in more detail below, as the knob 350 is turned, the stroke adjustment plug 340 is turned by the interaction of the first portion 352 of the knob 350 and the central bore 348 of the stroke adjustment plug 340. Thus, as the knob 350 is turned, the stroke adjustment plug 340 will be threaded up or down the central bore 300. The stroke adjustment plug 340 will slide on the first portion 352 of the knob 350 so that the knob 350 only needs to rotate and does not move up or down with respect to the central bore 300.

As illustrated in FIG. 3, the medicinal vial 104 comprises a cylindrical portion 400 having an inside diameter. A first end 402 of the cylindrical portion 400 is substantially closed with only a small opening 404 formed therein. A second end 406 of the cylindrical portion 400 proximate to the threaded portion 106 is open for the full inside diameter. A piston 410 is positioned within the cylindrical portion 400 through the second end 406. The piston 410 has a main body portion 412 sized to fit within the cylindrical portion 400 and to move freely therein. A first end 414 of the piston 410 extends from the cylindrical portion 400 for engagement with the piston 310, as described in more detail below. Preferably, as illustrated, the piston 410 comprises a solid plastic.

The piston 410 has a second end 418 which is positioned within the cylindrical portion 400. The second end 418 has an outside diameter smaller than the inside diameter of the cylindrical portion 400. A rubber piston ring 420 is positioned on the second end 418. The rubber piston ring 420 is sized to fit tightly within the cylindrical portion 400 to form a seal therein while still permitting movement within the cylindrical portion 400. Thus, as illustrated in FIG. 3, a liquid medicine 422 is constrained between the first end 402 of the cylindrical portion 400 and the rubber piston ring 420.

As further illustrated in FIG. 3, the opening 404 at the first end 402 of the cylindrical portion 400 is tapered such that the outer portion of the opening 404 at the outside surface of the cylindrical portion 400 has a diameter selected to control the flow of medicinal liquid from the cylindrical portion 400. For example, an opening 404 having a diameter of approximately 0.006 inch has been advantageous in one embodiment. The opening 404 is funnel shaped with its largest diameter inside the cylindrical portion 400 and its smaller diameter at the surface.

The second end 418 of the piston 410 has a central extended portion 430 which is aligned with the opening 404 in the cylindrical portion 400. The extended portion 430 has an outside diameter that is smaller than the inside diameter of the opening 404 within the cylindrical portion 400. However, the outside diameter of the extended portion 430 is greater than the inside diameter of the opening 404 at the surface. Preferably, the extended portion 430 has a funnel-shaped recess 432 formed therein so that the extended portion 430 has relatively thin walls at the end proximate to the opening 404 and has thicker walls proximate to the piston ring 420.

When the present invention is assembled as illustrated in FIGS. 1, 3 and 4, it operates to provide a high pressure needleless injection system. In operation, the vial 104 is first filled with an appropriate liquid medicine, such as, for example, insulin. The vial 104 is provided as a sterile one-use-only vial. In one embodiment, the vial 104 is filled in a pharmaceutical environment by dispensing an appropriate amount of the liquid medicine in the vial 104 and then inserting the piston 410 into the cylindrical body portion 400 to seal the liquid therein. The first end 402 is then sealed in an appropriate manner, and the filled vial 402 is packaged for distribution.

Alternatively, the vial 104 can be filled by a health care provider or, for self-injections of insulin and the like, by a patient. The vial 104 is shipped in sterile packaging (not shown). The vial 104 is removed from the sterile packaging and the first end 402 is inserted into a source of liquid medication. While holding the first end 402 of the vial 104 in the medication, the first end 414 of the piston 410 is pulled slowly to pull the piston 410 away from the first end 402 to thereby draw the liquid medicine into the vial 104 in a manner similar to filling a hypodermic syringe. The vial 104 is preferably filled initially with more than the desired volume of medication, and the excess volume will be ejected, as discussed below, prior to injecting the medication into the patient. In preferred embodiments, the vial 104 is provided with conventional markings 500 (FIG. 1) to indicate the volume of liquid in the vial 104. For example, the markings may be spaced to indicate 0.05 milliliter increments in volume. In a preferred embodiment, the vial 104 has a total volume of 0.5 milliliters and thus has ten markings thereon.

In a further alternative embodiment (not shown), the vial 104 can be distributed with a needle (not shown) attached to it so that it can be filled from sources of liquid medications which need to be punctured by a needle. See, for example, U.S. Pat. No. 4,680,027, which illustrates a removable needle. The needle is removed before engaging the vial 104 with the power mechanism 102.

Figure 5:
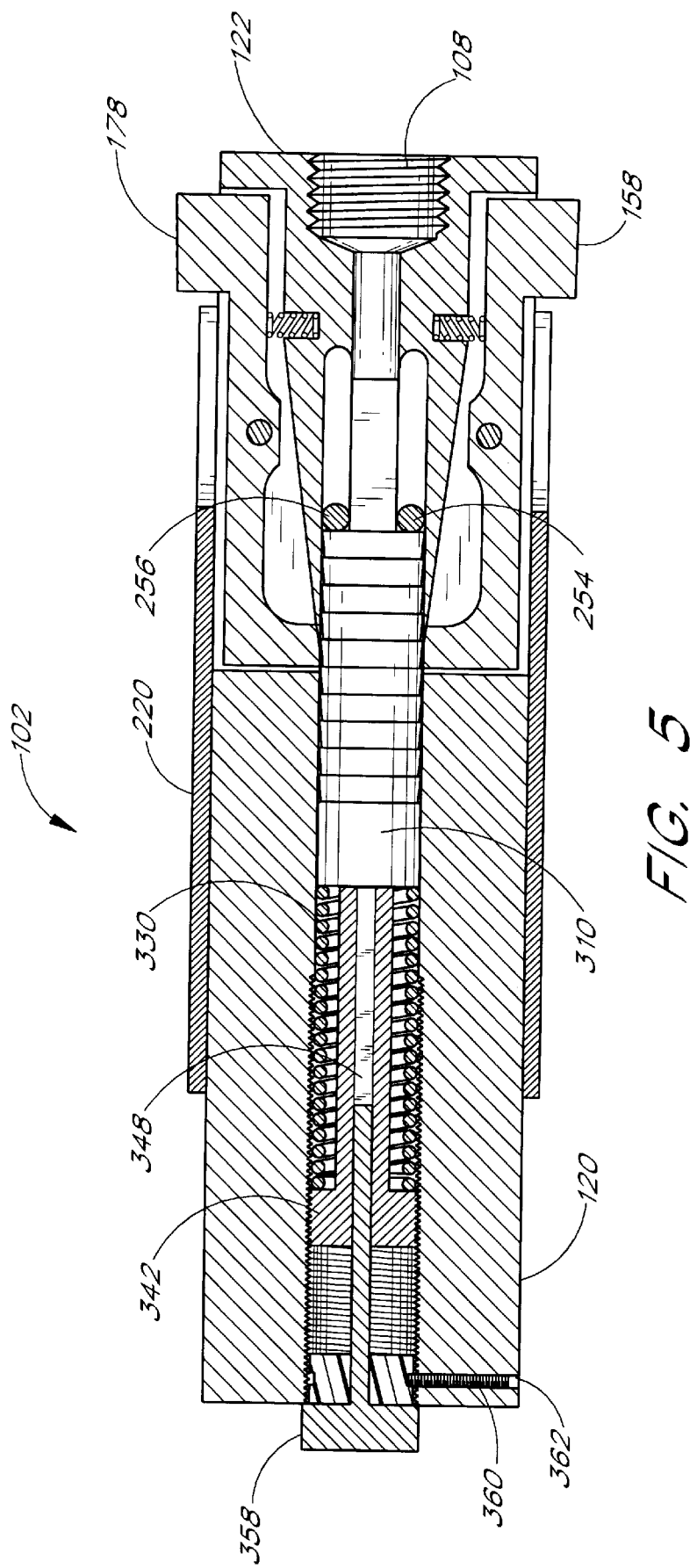
FIG. 5 is cross-sectional view of the needleless injector of FIG. 1, similar to the view of FIG. 3 but with the vial removed, which illustrates the action of cocking the power mechanism to prepare the injector to receive a vial having approximately half of the maximum volume of liquid medication.

Before engaging the vial 104 with the power mechanism 102, the power mechanism 102 is cocked to provide the pressure and stroke required to eject the liquid medication from the vial 104 for a particular volume of liquid medication. As illustrated in FIG. 5, this is accomplished by moving the cocking sleeve downward (in the direction from the top end 122 to the bottom end 124). The pins 254 and 256 are positioned proximate to the second end 314 of the piston 310 when the piston 310 is in its rest (uncocked) position. When the cocking sleeve 220 is moved toward the bottom end 124 of the body portion 120, the sleeve 220 causes the pins 254 and 256 to slide in the slots 200 and 204 against the force of the sleeve springs 202 and 206. The pins 254 and 256 push the piston 310 downwardly in the bore 300 toward the bottom end 124 of the body portion 120 against the pressure of the compression spring 330. As the piston 310 moves toward the bottom end 124, the ratchet ends 160 and 180 of the triggers 152 and 172 are forced outwardly by the taper of each ratchet 320 and then snap inward behind each shoulder 322. Thus, the ratchet ends 160 and 180 engage each shoulder 322 and operate to hold the piston 310 in position against the pressure of the compression spring 330.

The spacing between the shoulders 322 of the ratchets 320 is selected to provide a predetermined incremental increase in the volume of the vial 104 accommodated by the power mechanism 102. For example, in the preferred embodiment, each the distance between each shoulder 322 corresponds to a 0.05 milliliter increase in the volume of the vial 104. Thus, by listening to or feeling the interaction of the ratchet ends 160 and 180 with the ratchets 320, the user can cock the power mechanism to a distance corresponding to the desired volume of medicinal liquid to be ejected from the vial 104. In the preferred embodiment described herein, the power mechanism 102 includes an adjustment so that the user does not have to rely solely on counting the number of clicks. This feature is described below.

After the piston 310 has been moved to its cocked position, the cocking sleeve 220 is released and is returned to its original position, as shown in FIG. 1, by the pressure of the sleeve springs 202 and 206. The ratchet ends 160 and 180 of the triggers 152 and 172 hold the piston 310 in its cocked position.

When the vial 104 is inserted into the power mechanism 102, the first end 414 of the piston 410 contacts the second end 314 of the piston 310. If the vial 104 has been filled with more liquid than can be accommodated by the position of the piston 310, then, as the vial is screwed into the power mechanism 102, the first end 414 of the piston 410 will contact the second end 314 before the threaded portion 106 is fully seated in the socket 108. Thus, the piston 410 will move in the body portion 400 and force the excess liquid out of the vial 104.

Figure 6:
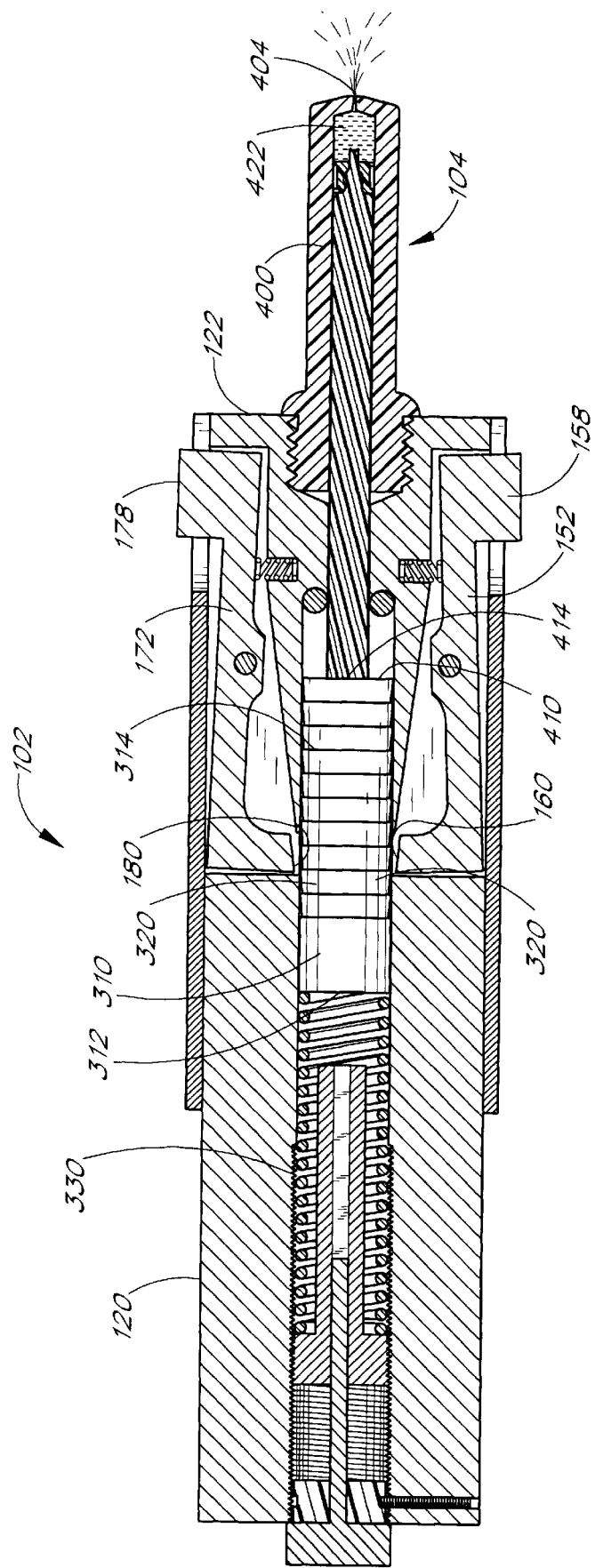
FIG. 6 is a cross-sectional view of the needleless injector of FIG. 1, similar to the view of FIG. 3, showing the ejection of the liquid medication when the piston is moved by the springs.

As illustrated in FIG. 6, when the activation portions 158 and 178 of the triggers 152 and 172 are pressed by the user, the ratchet portions 160 and 180 are disengaged from the ratchets 320. The pressure of the compression spring 330 operates against the first end 312 of the piston 310 to force the piston 310 toward the upper end 122 of the body portion 120. The second end 314 of the piston 310 operates against the first end 414 of the piston 410 to force the piston 410 further into the body portion 400 of the vial 104 and thereby force the liquid medication 422 out of the vial 104 through the opening 404 as illustrated in FIG. 6.

By providing the two opposing triggers 152 and 172, the power mechanism 102 of the present invention requires the user to press both activation portions 158 and 178 to release the piston 310. This safety feature reduces the likelihood that the power mechanism 102 will be accidentally triggered before the user has the vial 104 in place on the patient's skin and is ready to trigger the mechanism.

When the piston 310 has moved to its full length of travel, the forward motion of the piston 310 is stopped by metal outcroppings 510 which remain after forming the middle portion 306 of the central bore 300 and which extend above and below the middle portion 306 between the two slots 200 and 204. Because of the location of the section lines 4—4 in FIG. 1A, the outcroppings 510 are shown in phantom in FIG. 4. The outcroppings 510 prevent the second end 314 of the piston 310 from striking the pins 254 and 256 when the piston 310 reaches the end of its travel.

As further illustrated in FIG. 7, when the end 402 of the vial 104 is pushed against the skin 600 of a patient and the triggers are activated, the liquid is forced out of the opening 404 with sufficient force to penetrate the skin 600 of a patient and to penetrate the tissues 602 beneath the skin 600. As illustrated in FIG. 8 and FIG. 9, when the liquid has been fully expelled from the vial 104 as the piston 410 travels to the end of the body portion 400, the extended portion 430 enters the funnel shaped inside portion of the opening 404. The relatively thin walls of the extended portion 430 caused by the funnel-shaped recess 432 engage the inside walls of the hole 404 and force the hole 404 closed. The vial 104 and the piston 410 are preferably formed from medical-grade plastic. The force of the engagement between the extended portion 430 and the inner wall of the hole 404 is sufficient to cause the two parts to mesh, thereby effectively preventing the vial 104 from being reused.

As discussed above, it is preferred that the power mechanism 102 be cocked so that the first end 414 of the piston 410 just engages the second end 314 of the piston 310 when the vial 104 is inserted into the power mechanism 102. If, the power mechanism is not cocked far enough, a portion of the liquid medication will be forced out of the vial 104 as the vial 104 is inserted into the socket 108, thus reducing the medication to less than the proper dosage. If, on the other hand, the power mechanism is cocked too far, the first end 414 of the piston 410 will not touch the second end 314 of the piston 310. Thus, when the triggers 152 and 172 are activated, the piston 310 will travel a short distance and will be traveling a significant velocity before engaging the first end 414 of the piston 410. This can have the undesirable effect of causing the piston 310 to slap against the first end 414 of the piston 410 and may cause the user to fail to hold the end 402 of the vial 104 against the skin. Thus, the liquid medication 422 may tend to spray on the skin rather than to penetrate the skin as desired.

The present invention includes a mechanism to reproducibly match the position of the cocked piston 310 to the first end 414 of the piston 410. In particular, the stroke adjustment plug 340 permits the user to set the stroke of the piston 310 to the precise amount of the liquid medication to be dispensed so that when the vial 104 is engaged with the power mechanism 102, the first end 414 of the piston 410 will rest on the second end 314 of the piston 310. Thus, when the power mechanism 102 is triggered, the piston 310 will accelerate the piston 410 to smoothly force the liquid medication 422 out of the opening 404.

Figure 10:
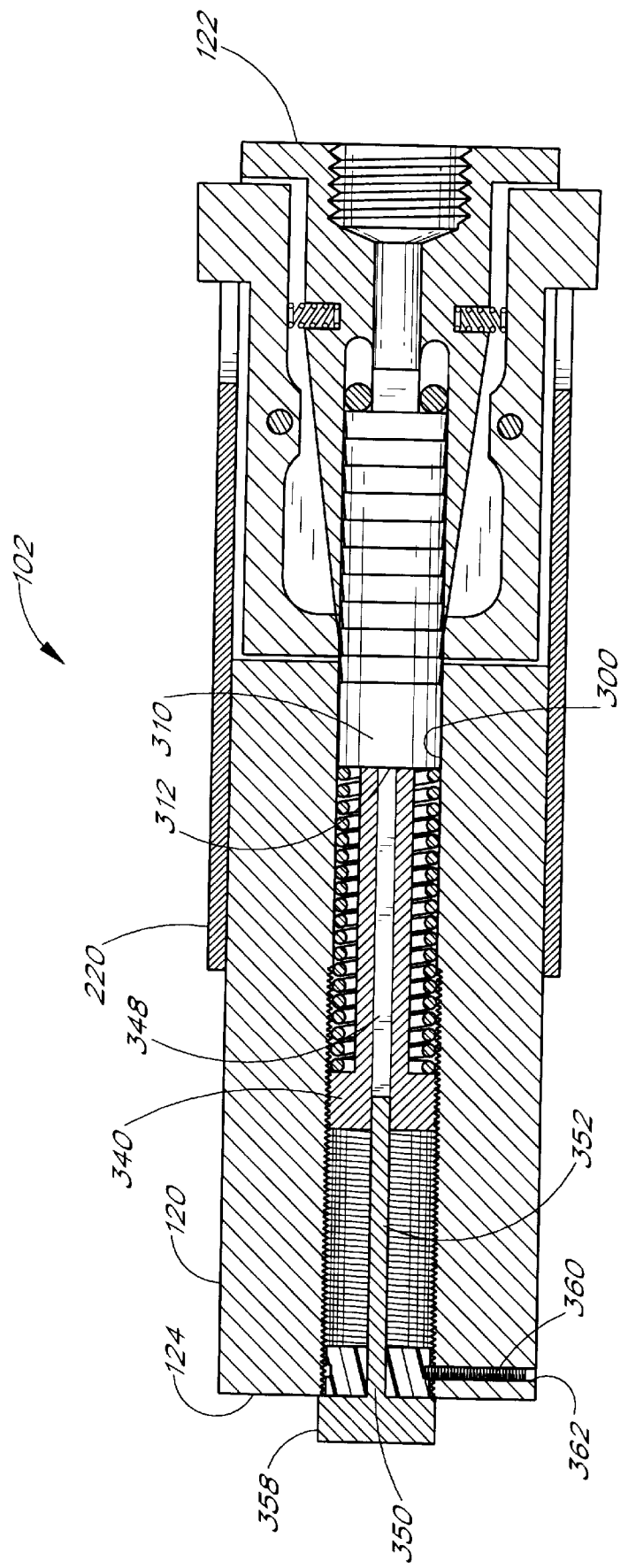
FIG. 10 is a cross-sectional view of the needleless injector similar to FIG. 3, showing the dose adjustment stop moved to permit only a vial having a small dose of liquid medicine to be inserted into the needleless injector.

As illustrated in FIG. 10, the stroke adjustment plug 340 is shown in a position so that the piston 310 can be moved by only the distance of two ratchets. The user places the stroke adjustment plug 340 in the position of FIG. 10 by turning the knurled knob 358 clockwise with respect to the bottom end 124 of the body portion 120. The stroke adjustment knob 350 turns within the central bore 300 causing the first portion 352 (i.e., the square bar) to turn. The first portion 352 is engaged with the central bore 348 of the stroke adjustment plug 340. Thus, as the stroke adjustment knob 350 turns, the stroke adjustment plug 340 turns within the central bore 300. The threaded engagement of the stroke adjustment plug 340 with the central bore 300 causes the stroke adjustment plug 340 to advance toward the top end 122 of the body portion 120 to the position shown in FIG. 10. The user can readily determine the correct position to place the stroke adjustment plug 340 by cocking the power mechanism 102 the required number of clicks (e.g., one click for 0.05 milliliters of medication, two clicks for 0.1 milliliter of medication, and so on). While the piston 310 is maintained in the cocked position, the stroke adjustment knob 350 is turned until the user feels resistance when the stroke adjustment plug 340 engages the first end 312 of the piston 310. The stroke adjustment plug 340 is then left in this position. Thus, each time the power mechanism 102 is cocked by moving the cocking sheath 220 toward the bottom end 124, as shown, the piston 310 cannot be ratcheted beyond the position established by the stroke adjustment plug 340.

Figure 11:
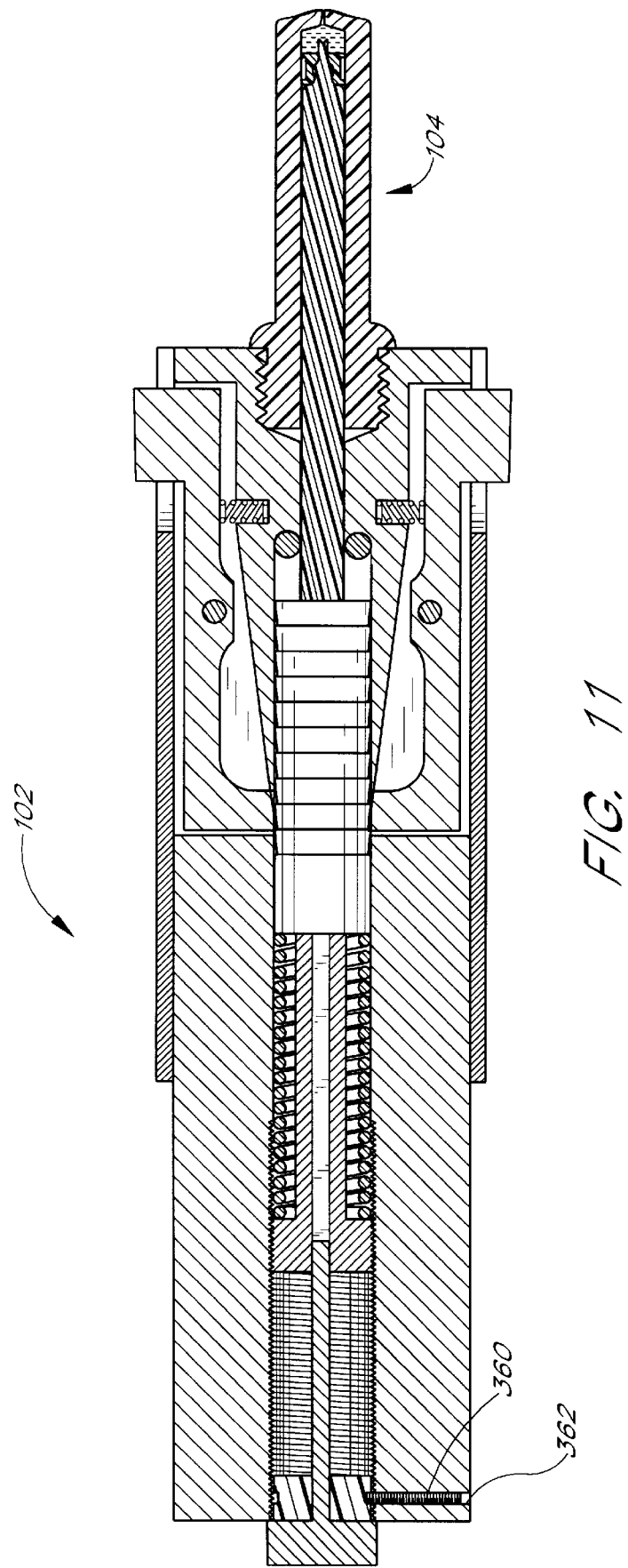
FIG. 11 is a cross-sectional view of the needleless injector of FIG. 10 with the vial of liquid medicine in position to be ejected.

When the vial 104 is engaged with the power mechanism 102 when adjusted as in FIG. 10, the vial 104 can hold a maximum of 0.1 milliliters as illustrated in FIG. 11. Any excess medication will be ejected as the vial 104 is engaged, as discussed above.

In the event that the user does not want to make further adjustments to the stroke of the power mechanism 102, the stroke adjustment knob 350 may be removed by retracting the screw 360, or, in the alternative, the screw 360 may be further engaged in the hole 362 until the end of the screw 360 frictionally engages the groove 356 so that the knob 350 cannot be turned.

Figure 12:
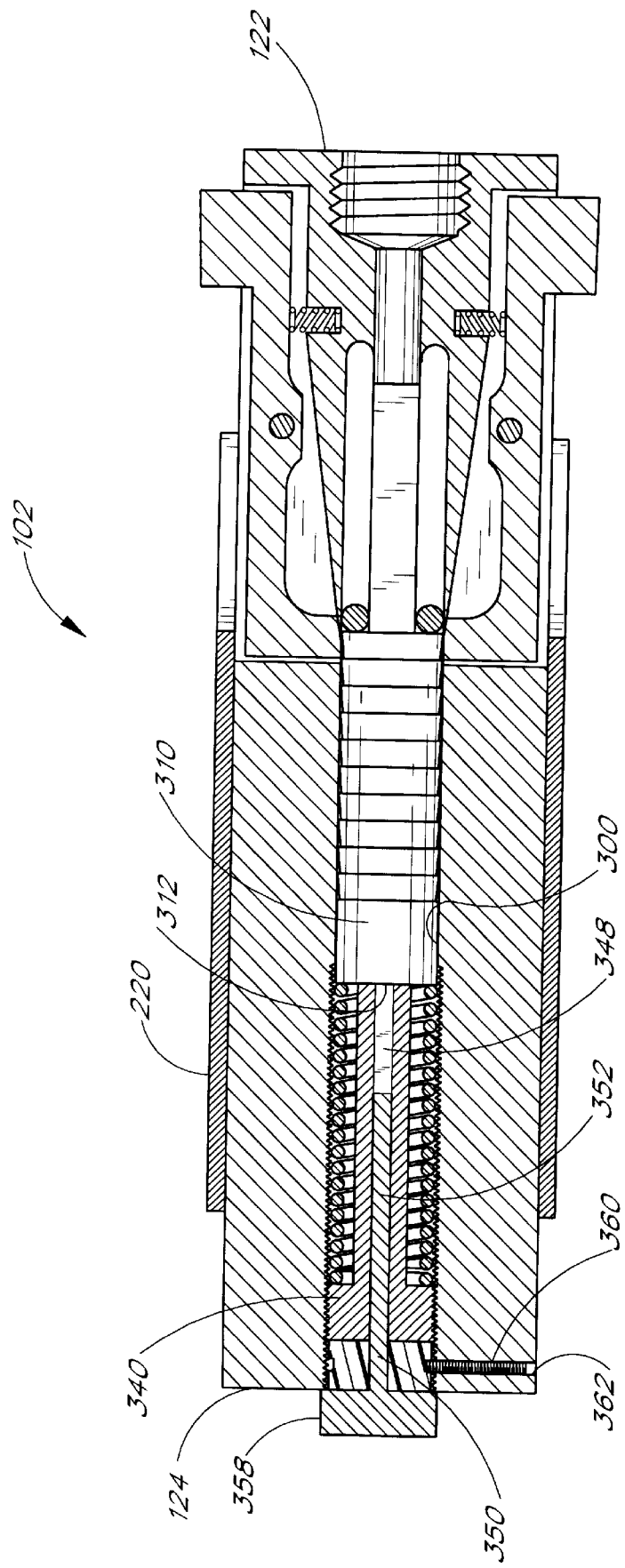
FIG. 12 is a cross-sectional view of the needleless injector similar to FIG. 3, showing the dose adjustment stop moved and the injector cocked to permit a vial having a maximum dose of liquid medicine to be inserted into the needleless injector.
Figure 13:
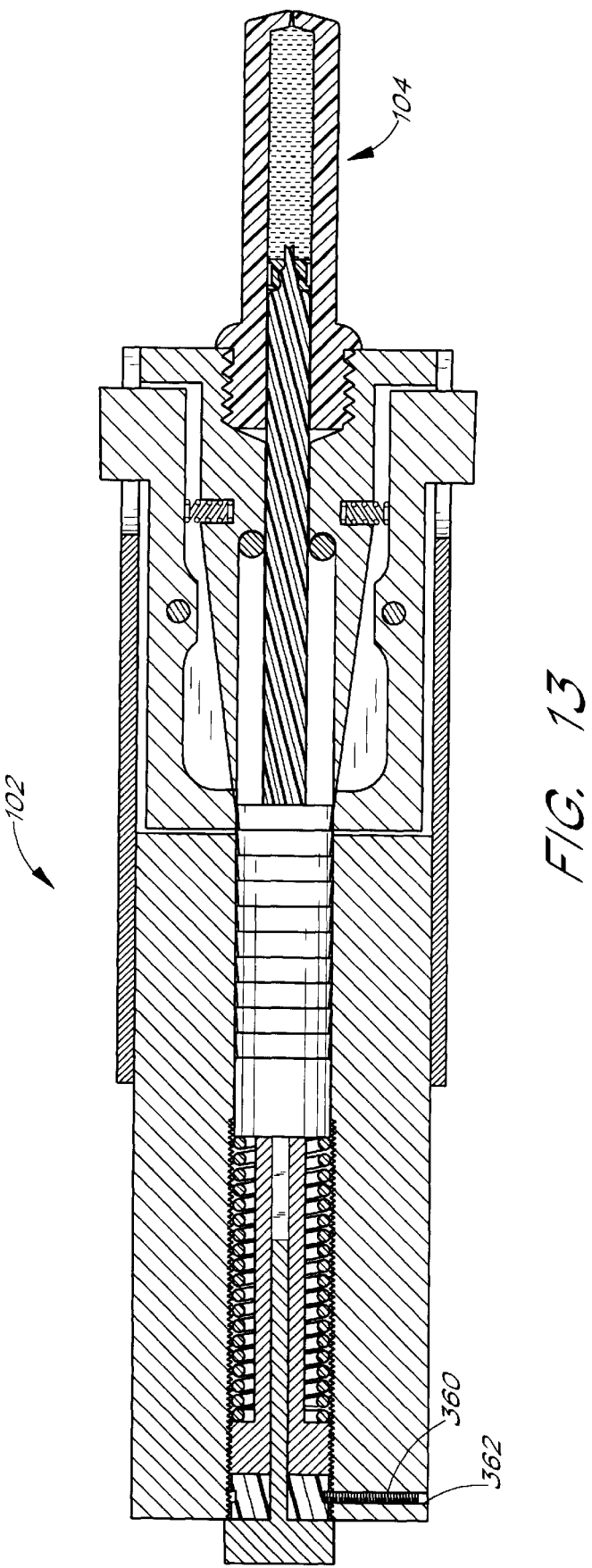
FIG. 13 is a cross-sectional view of the needleless injector of FIG. 12 with the vial of liquid medicine in position to be ejected.

FIG. 12 further illustrates the adjustment of the present invention, wherein the stroke adjustment plug 340 is positioned for maximum discharge of medication (e.g., 0.5 milliliter). FIG. 13 illustrates the vial 104 in position in the power mechanism 102 when the power mechanism 102 has been cocked as illustrated in FIG. 12.

The stroke adjustment plug 340 has the further advantage that the force applied to the liquid medication for the initial injection of the medication through the skin is substantially the same regardless of the volume of the liquid to be ejected. In particular, as illustrated in FIGS. 6, 11 and 13, the compression spring 330 is compressed by substantially the same amount between the first end 312 of the piston 310 and the first portion 342 of the stroke adjustment plug 340. Thus, when the piston 310 is first released, the force initially applied to the piston 310 and thus to the liquid medication 422 is substantially the same for each volume.

Figure 16:
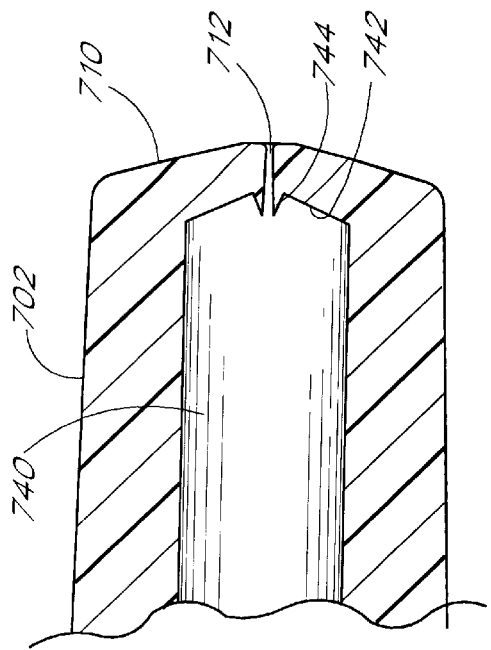
FIG. 16 is an enlarged cross-sectional view of a portion of the vial showing the modified orifice and the protuberance surrounding the inner portion of the orifice.
Figure 14:
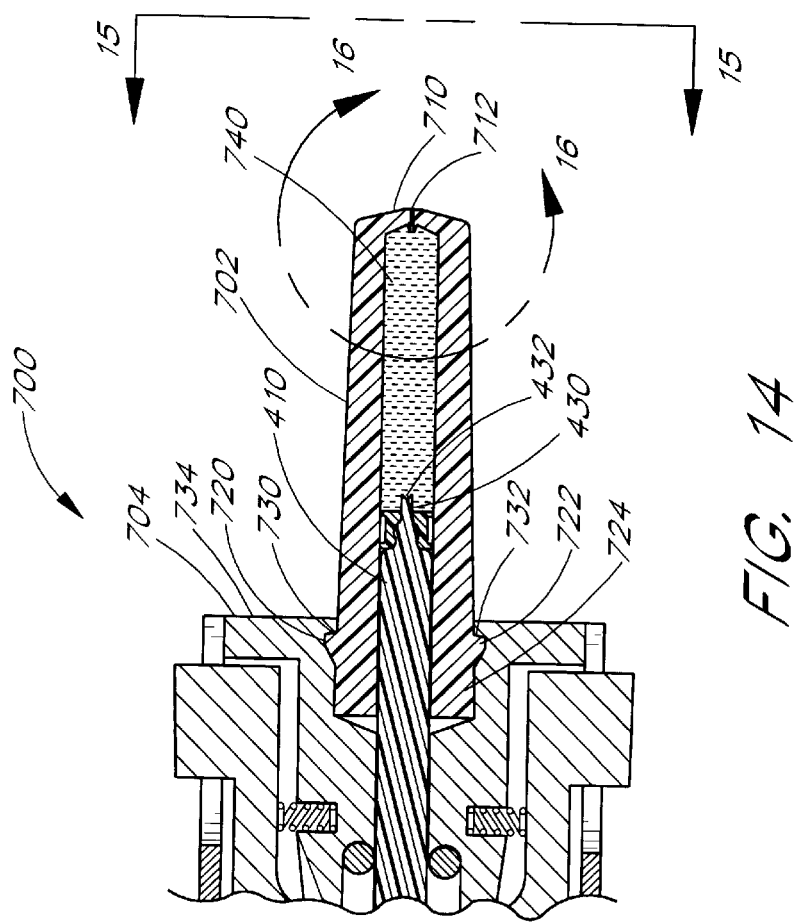
FIG. 14 is a cross-sectional view of an alternative embodiment of the needleless injector having a quarter-turn engagement mechanism between the vial and the power mechanism, and further having a modified orifice.

The needleless injector of the present invention can be manufactured in other configurations. For example, FIGS. 14–17 illustrated an alternative embodiment of the needleless injector 700 in which a vial 702 can be more quickly engaged onto a power mechanism 704. The embodiment of FIGS. 14–17 further includes a modified first end 710 of the vial 702 to assure that an orifice 712 is fully closed after the vial is emptied. Other than as described herein, the embodiment 700 of FIGS. 14–16 is substantially similar to the previously described embodiment, and like elements are numbered the same.

Figure 15A:
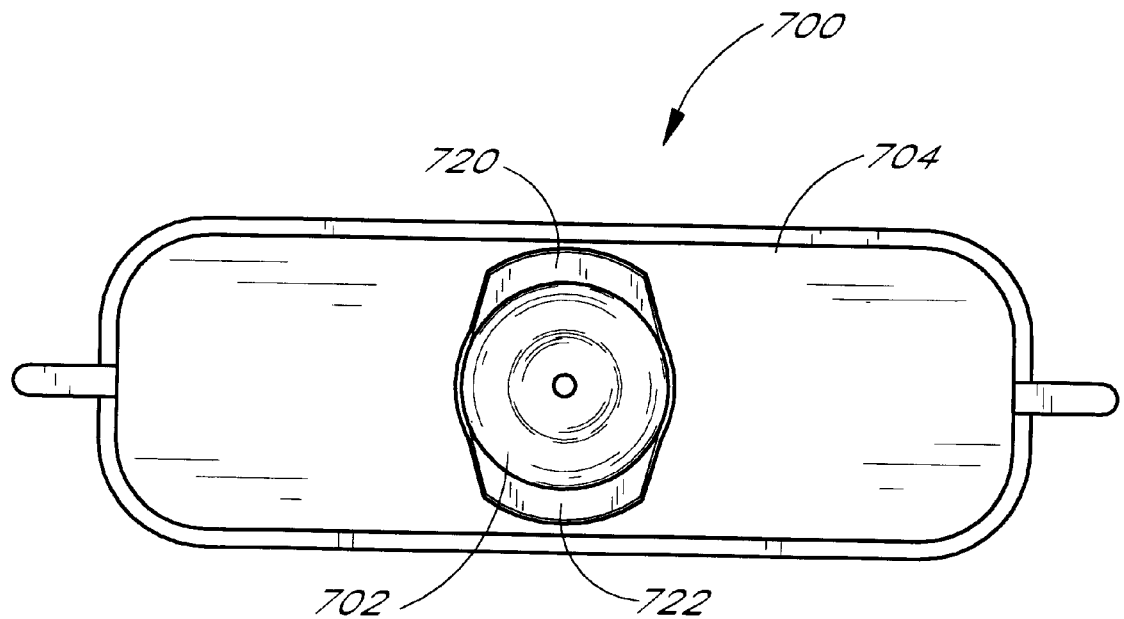
FIG. 15A is a front elevational view of the needleless injector of FIG. 14 showing the positioning of the vial onto the power mechanism prior to turning the vial to lock the vial to the power mechanism.
Figure 15B:
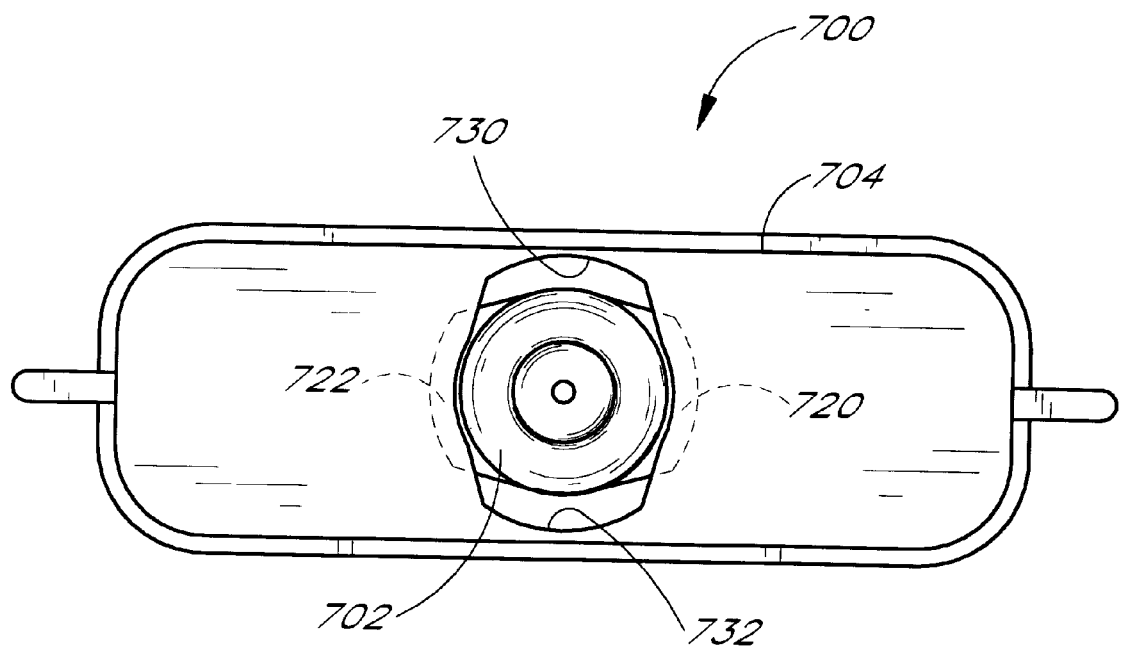
FIG. 15B is a front elevational view of the needleless injector of FIG. 14 showing the positioning of the vial after turning the vial to lock the vial to the power mechanism.

As illustrated in the cross-sectional view of FIG. 14 and in the front elevational views in FIGS. 15A and 15B, the vial 702 engages the power mechanism 704 via a quarter-turn engagement mechanism comprising a first thread 720 and an oppositely disposed second thread 722 formed on a second end 724 of the vial 702. Each of the threads 720 and 722 extends for approximately one-fourth of the circumference of the second end 724 of the vial 702. The threads 720 and 722 have pitches selected to match corresponding threads 730 and 732 formed in a first end 734 of the power mechanism 704. The threads 730 and 732 are conventional double lead threads which enable both threads 720 and 722 of the vial 702 to be engaged at the same time. By turning the vial 702 one-quarter turn in the clockwise direction, as viewed in FIGS. 15A and 15B, the vial 702 is fully engaged with the power mechanism 704, thus enabling the user of the present invention to rapidly switch vials. This feature is particularly advantageous for mass inoculations of vaccine, and the like.

Figure 17:
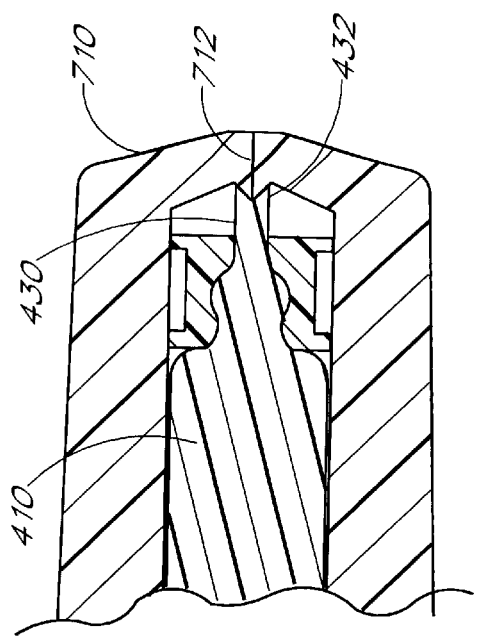
FIG. 17 further illustrates the enlarged cross-sectional view of FIG. 16 and shows the engagement of the funnel-shaped recess on the piston with the protuberance around the orifice to squeeze the orifice closed when the piston is driven forward.

As illustrated more clearly in the enlarged view of FIG. 16, the vial 702 in accordance with the embodiment of FIGS. 14–16 has the modified orifice 712. In particular, the orifice 712 extends into a cavity 740 of the vial 702. An inner wall 742 of the vial 702 is formed into a conical protuberance 744 which surrounds the innermost portion of the orifice 712. The conical protuberance 744 is sized to have a initial outside diameter greater than the inside diameter of the funnel-shaped recess 432 on the extended portion 430 of the piston 410. Thus, when the piston 410 is driven forward by the power mechanism 704, the funnel-shaped recess 432 engages the outside of the conical protuberance 744 and squeezes the orifice 712 closed, as illustrated in FIG. 17.

As further illustrated in FIG. 16, the inner wall 742 of the vial 702 proximate to the orifice 712 is sloped generally toward the orifice 712, and the protuberance 744 extends from the sloped portion of the inner wall 742.

In one embodiment of the present invention, the various portions of the power mechanism 102 are fabricated from aluminum or other suitable metal, as indicated in cross-section herein. Alternatively, the power mechanism 102 may be fabricated from high impact plastic to reduce the cost and the weight of the mechanism. Preferably, the vial 104 and its component elements are fabricated from a medical grade plastic such as is conventionally used in hypodermic syringes and the like.

The invention may be embodied in other specific forms without departing from its spirit or essential characteristics. The described embodiments are to be considered in all respects only as illustrative and not restrictive. The scope of the invention is therefore indicated by the appended claims rather than by the foregoing description. All changes which come within the meaning and range of equivalency of the claims are to be embraced within that scope.

What is claimed is:

1. A medication vial for a needleless injection of a liquid medication into a patient, said medication vial comprising:

a container defining a volume which receives a quantity of liquid medication, said container having a first end and a second end, said first end having an orifice formed therein to release said liquid medication; and a piston which moves within said container, said piston having a first end and a second end, said first end moveable with respect to said first end of said container to define said volume when said first end of said piston is moved away from said first end of said container, said piston forcing said liquid medication through said orifice when said first end of said piston is moved toward said first end of said container, said first end of said piston having a protuberance formed thereon, said protuberance closing said orifice by squeezing said orifice closed.

2. The medication vial as defined in claim 1, wherein:

said orifice has a protuberance surrounding an innermost portion thereof; and said protuberance of said piston engages said protuberance surrounding said orifice to close said innermost portion of said orifice.

3. The medication vial as defined in claim 1, wherein:

said orifice has an enlarged innermost portion thereof; and said protuberance of said piston enters said enlarged innermost portion of said orifice to close said orifice.

4. The medication vial as defined in claim 1, wherein:

said first end of said container comprises an outside surface and an inside surface;

said orifice comprises a bore formed through said first end of said container between said inside surface and said outside surface;

said inside surface has a protuberance having an outer wall, said bore extending through said protuberance of said inner surface; and said protuberance of said piston squeezes said orifice closed by engaging said outer wall of said protuberance of said inner surface and compressing said outer wall.

5. The medication vial as defined in claim 1, wherein said orifice comprises a bore formed through said first end of said container, said bore defined by an inner wall, and wherein said protuberance closes said orifice by engaging said inner wall of said bore to force the inner wall closed.

* * * * *